United States Patent [19]
Fenton, Jr. et al.

[11] Patent Number: 5,190,520
[45] Date of Patent: Mar. 2, 1993

[54] REINFORCED MULTIPLE LUMEN CATHETER

[75] Inventors: Paul V. Fenton, Jr., Marblehead; William J. Gorman, Newburyport; Thomas M. Young, North Andover, all of Mass.

[73] Assignee: Strato Medical Corporation, Beverly, Mass.

[21] Appl. No.: 595,028

[22] Filed: Oct. 10, 1990

[51] Int. Cl.⁵ ............................................ A61M 25/00
[52] U.S. Cl. ...................................... 604/43; 604/282
[58] Field of Search ...................... 604/29, 43, 53, 264, 604/280, 282; 138/111, 115–117

[56] References Cited

U.S. PATENT DOCUMENTS

| | | |
|---|---|---|
| 419,926 | 1/1990 | Chapman . |
| 2,211,975 | 3/1937 | Hendrickson ...................... 128/349 |
| 3,598,126 | 8/1971 | Hoeltzenbein ...................... 128/348 |
| 4,044,765 | 8/1977 | Kline ................................ 128/214.4 |
| 4,106,506 | 8/1978 | Koehn et al. ..................... 128/214.4 |
| 4,134,402 | 1/1979 | Mahurkar ........................ 128/214 R |
| 4,203,436 | 5/1980 | Grimsrud ........................ 128/214 R |
| 4,256,146 | 3/1981 | Genini et al. ......................... 138/111 |
| 4,368,730 | 1/1983 | Sharrock ............................. 604/158 |
| 4,385,631 | 5/1983 | Uthmann ............................. 604/284 |
| 4,498,473 | 2/1985 | Gereg ............................... 128/207.15 |
| 4,508,535 | 4/1985 | Joh et al. ............................. 604/282 |
| 4,543,087 | 9/1985 | Sommercorn et al. ............... 604/43 |
| 4,547,192 | 10/1985 | Brodsky et al. ..................... 604/270 |
| 4,581,012 | 4/1986 | Brown et al. ......................... 604/43 |
| 4,619,643 | 10/1986 | Bai ....................................... 604/43 |
| 4,634,432 | 1/1987 | Kocak ................................. 604/167 |
| 4,639,252 | 1/1987 | Kelly et al. .......................... 604/282 |
| 4,676,229 | 6/1987 | Krasnicki et al. ....................... 128/4 |
| 4,719,924 | 1/1988 | Crittenden et al. ................. 128/772 |
| 4,737,153 | 4/1988 | Shimamura et al. ................ 604/282 |
| 4,805,155 | 2/1989 | Mahurkar ............................ 604/43 |
| 4,832,681 | 5/1989 | Lenck ................................... 600/34 |
| 4,846,791 | 7/1989 | Hattler et al. ........................ 604/43 |

Primary Examiner—John D. Yasko
Assistant Examiner—Anthony Gutowski
Attorney, Agent, or Firm—Lahive & Cockfield

[57] ABSTRACT

Disclosed is a flexible, reinforced, multiple lumen catheter. This catheter includes an elongated, flexible, tubular element extending about a central axis, and including embedded therein at least one filament extending in a helical path about the central axis. The inner surface of the tubular element defines an interior region. The catheter also includes an elongated divider element having elongated lateral edges. These edges are integral with, and extending from, portions of the inner surface of the tubular element. At least two lumens are defined in the interior region of the tubular element on opposing sides of the divider element. Also disclosed is a method for assembling the flexible, reinforced, multiple lumen catheter.

12 Claims, 2 Drawing Sheets

REINFORCED MULTIPLE LUMEN CATHETER

BACKGROUND OF THE INVENTION

This invention relates to accessing body fluids for diagnostic and therapeutic purposes, and in particular, to a catheter for venous vascular access. More specifically, this invention relates to a reinforced dual lumen catheter for hemodialysis or apheresis procedures requiring bidirectional blood flow.

Extracorporeal treatment of blood requires that the vascular system of a subject be directly accessed, and that the blood be removed and then returned to the subject after removal of various components or toxins, or after addition of oxygen. Extracorporeal treatments include apheresis, or the collection of blood cells, the removal of a specific blood cell type from the blood, or plasma exchange, and hemodialysis, or the removal of various chemical substances from the blood including ingested or injected drugs, or toxins created during normal body metabolism, the presence of which is most often due to renal impairment.

Traditionally, such extracorporeal treatments involves the tapping of the vascular system via a first needle attached to a first catheter. The blood is then circulated through a treatment device, and then returned to the vascular system via a second catheter and needle. This technique requires that the needles be spaced a sufficient distance apart so that treated blood will not reenter the output needle for additional treatment. Adequate needle spacing is also required to prevent collapse of the accessed vein. The problem of vascular collapse becomes compounded if the treatment is one which must be repeated and the vein or fistula becomes weakened with repeated punctures.

Another method of performing extracorporeal blood treatment includes the use of a single needle and catheter accommodating bidirectional flow through which the blood is removed and returned. See, for example, the simple double lumen cather disclosed by Mahurkar in U.S. Pat. No. 4,808,155; a double lumen needle and cannula also disclosed by Mahurkar in U.S. Pat. No. 4,134,402; a dual channeled hypodermic needle disclosed by Grumarud in U.S. Pat. No. 4,203,436; and a hemodialysis catheter with two circular lumens arranged side by side disclosed by Uthmann in U.S. Pat. No. 4,385,631. This method minimizes insertion trauma and reduces potential for clotting. However, this method may not be of use to all patients as flow rates within the needle are limited. In addition, prerequisite to this technique is an intermittent occlusion machine capable of cyclical operation.

A common problem encountered in the extracorporeal treatment of blood is collapse of the catheter due to decreased pressure within the catheter, and subsequent weakening of the catheter walls. Single lumen catheters and tubes have long been reinforced to reduced collapse. See, for example, U.S. Pat. No. 419,926 granted to Chapman in 1890, and U.S. Pat. No. 2,211,975 granted to Hendrickson in 1937; and more recently U.S. Pat. Nos. 4,832,681, 4,737,153, and 4,639,252.

Hence there is a long felt need for a vascular access catheter which will not collapse, which accommodates dual flow therethrough with a sufficient flow rate, and the use of which causes minimal clotting and recycling of treated blood.

Accordingly, it is an object of the present invention to provide an improved catheter allowing for plural flow therein.

It is another object of the invention to provide a reinforced multiple lumen catheter which will not collapse.

Yet another object of the invention is to provide a method of fabricating a reinforced, multiple lumen catheter.

SUMMARY OF THE INVENTION

Briefly, the present invention is directed to a multiple lumen catheter for blood treatment. It has been discovered that a flexible, multiple lumen catheter which is reinforced will not collapse, and has a reduced potential to form clots within the tube. Neither does this catheter lend itself to leakage at the point of insertion in the body. In addition, this multiple lumen catheter has a reduced potential to recycle blood while providing a high flow rate of blood therethrough.

The catheter includes an elongated, flexible, tubular element extending about a central axis, and whose inner surface defines an interior region. Preferably, this tubular element is composed of a material selected from the group consisting of natural rubber, synthetic rubber and thermoplastics. In some embodiments of the invention, the tubular element includes silicone or a thermal plastic selected from the group consisting of polyurethane and polyvinylchloride. A preferred synthetic rubber is butylstyrene.

Embedded in the tubular element is a filament extending in a helical path about the central axis. In preferred aspects of the invention, the filament is composed of a metal such as surgical grade stainless steel, titanium, or a plastic such as polyester or polyamide.

The catheter also includes an elongated divider element having elongated lateral edges which are integral with, and extend from, portions of the inner surface of the tubular element. In this way, at least two lumens are defined in the interior region on opposing sides of the divider element.

In one form, the divider element is substantially rectangular, and thus defines two distinct lumens. In alternative embodiments, the divider element has a substantially Y-shaped cross-section, thereby defining three lumens in the interior region. Similarly, the divider element may be X or star-shaped, thereby defining four or more lumens in the interior region.

In one embodiment of the invention, the tubular element includes two concentric components. The first is an elongated, flexible, tubular sheath having a substantially circular cross-section and an inner diameter substantially equal to D. The second component is an elongated, flexible, tubular interior element having an outer surface, an interior surface, and a substantially circular cross-section, all disposed concentrically within the first component. The outer surface of the second component has a diameter equal to D1 and the interior surface has a diameter equal to d, where D1 is less than D, and d is less than D1. In this configuration, the interior surface of the interior element forms the inner surface of the tubular element. The tubular element further includes a filament wound about the outer surface of the tubular interior element. A flexible bonding material is disposed in the region between the outer surface of the interior element and the inner surface of the sheath.

Another embodiment of the invention is a method of assembling the reinforced, multiple lumen catheter.

This method includes extruding a first material to establish elongated, flexible, tubular sheath extending along a central axis. Also extruded is a second material which establishes a flexible, multiple lumen interior element extending along a central axis. An axial stretching force is applied to stretch the interior element in the direction of the central axis, whereby the outer diameter of the interior element is reduced to be less than D1. The stretched interior element is then drawn through the interior of at least one filament. The filament is formed in the shape of a helix having an inner diameter substantially equal to D1. The stretching force is then removed from the interior element. At this point, the interior element and the helical filament are in intimate contact, thereby establishing a filament-wound, multiple lumen interior element. The exterior of this element is coated with an adhesive. The sheath is then positioned over the adhesive coated element and the adhesive is then cured.

In preferred aspects of the invention, the adhesive includes the same material of which the tubular element is formed. The method may further include the step of shaping the distal end of the catheter to produce a formed tip. In addition, the step of dividing a proximal end of the catheter to establish at least a first tubular portion including one of the lumens and a second tubular portion including the other of the lumens, may be provided. In yet another embodiment of the method of the invention, the sheath may be expanded by exposing it to freon before the sheath is positioned over the adhesive-coated, filament-wound catheter.

BRIEF DESCRIPTION OF THE DRAWING

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
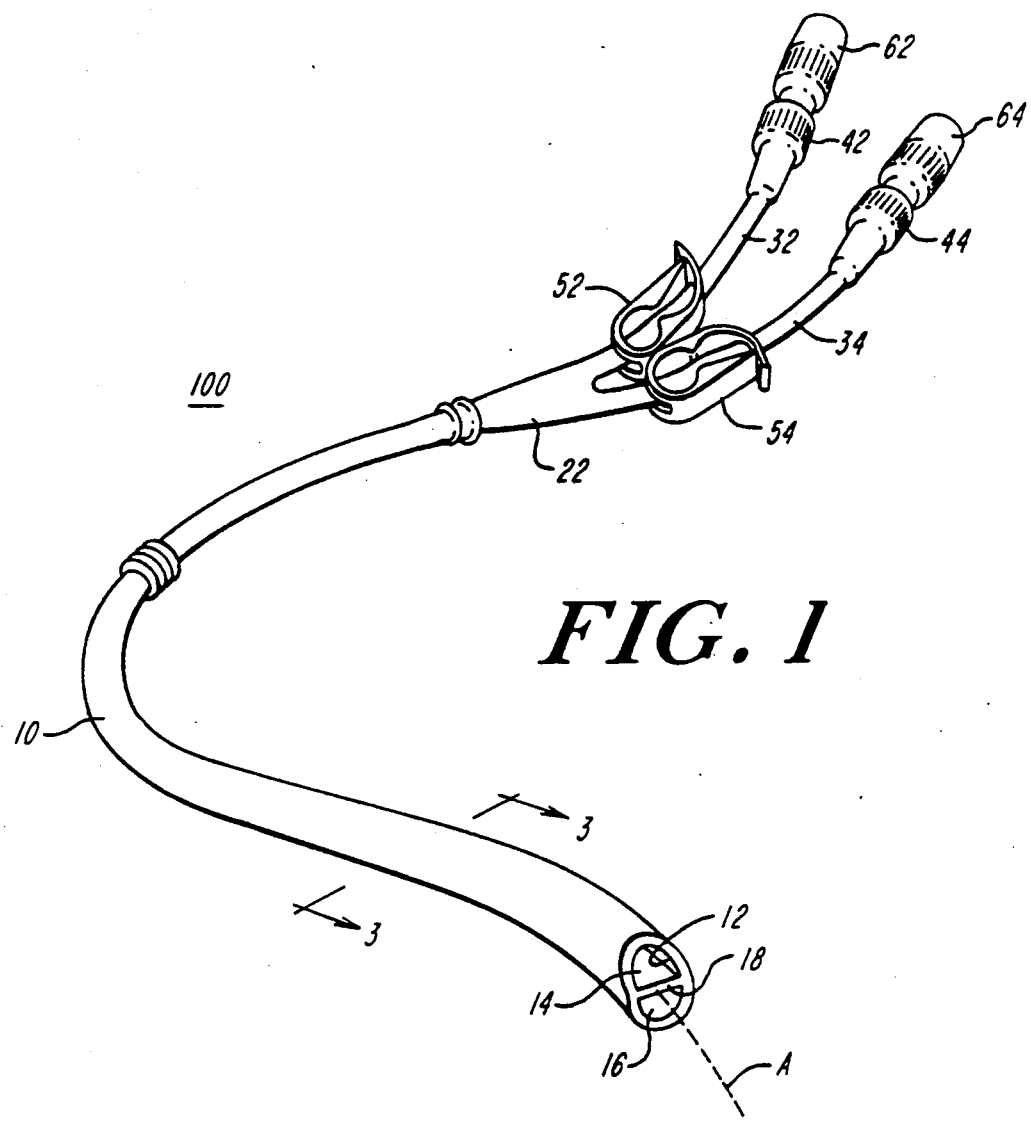
FIG. 1 is a perspective view of a flexible, reinforced, dual-lumen catheter having a bifurcated proximal external portion terminating in luer lock connections useful for insertion into a hemodialysis or apheresis device.
Figure 2:
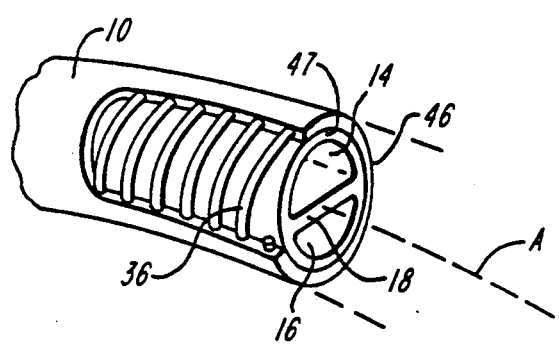
FIG. 2 is a partially cut away view of a portion of the catheter of FIG. 1 showing the wire reinforcement.
Figure 3:
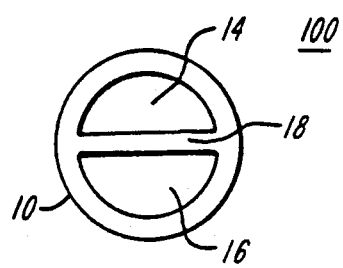
FIG. 3 is a cross-sectional view along lines 3—3 of FIG. 1.

FIGS. 1—3 refer to various views of a reinforced, flexible, dual lumen catheter 100. FIG. 1 shows a perspective view of catheter 100 including tubular element 10 extending about central axis A, and having inner surface 12 defining interior region 20. In the illustrated embodiment, element 10 includes an outer cylindrical sheath 46 concentrically positioned over an inner, generally cylindrical element 47. In alternative embodiments, element may be an integral one-piece element.

A substantially rectangular divider element 18 has elongated lateral edges integral with, and extending from, portions of the inner surface 12 of tubular element 10. Divider element 18 defines Lumens 14 and 16 in interior region 20 on opposing sides of divider element 18. In this embodiment, proximal portion 22 of tubular element 10 bifurcates into extension tubes 32 and 34, and terminates in two female threaded luer lock connectors 42 and 44. Extension tubes 32 and 34 are equipped with clamp closures 52 and 54, respectively and removable gum injection ports 62 and 64. Clamp closures 52 and 54 may be color coded or otherwise labelled to distinguish venous (return) flow from arterial (outflow).

Tubular element 10 is composed of a material selected from the group consisting of natural rubber, synthetic rubber and thermoplastics. For example, silicone or a thermal plastic selected from the group consisting of polyurethane and polyvinylchloride are useful. A preferred synthetic rubber is butylstyrene.

FIG. 2 is a partially cut away view of a portion of catheter 100 of FIG. 1 showing wire reinforcement filament 36 embedded in tubular element 10 and extending in a helical path about central axis A. Filament 36 may be composed of a metal, such as surgical grade stainless steel or titanium, or a plastic, such as polyester or polyamide.

Figure 4:
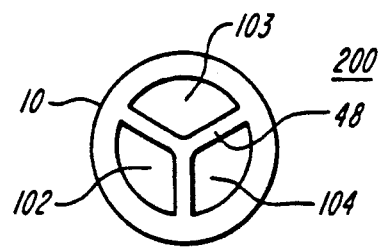
FIG. 4 is a cross-sectional view of a tri-lumen catheter.

The divider element 18 is shown in FIG. 3 as substantially ribbon-shaped or rectangular, whereby two lumens, 14 and 16, are defined in interior region 20. Alternatively, the divider element 48 within multiple lumen catheter 200 shown in FIG. 4 has a Y-shaped cross-section, thereby defining lumens 102, 103, and 104. This divider element may be composed of the same material as the tubular element.

Figure 5:
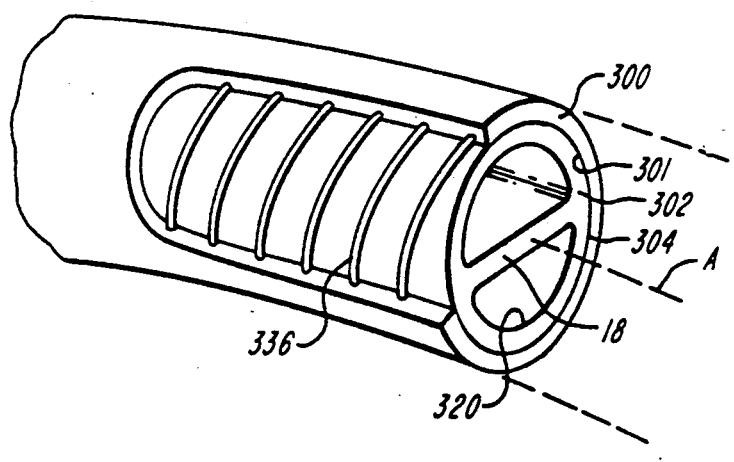
FIG. 5 is a partially cut-away view of a portion of another embodiment of the invention.

In another form of the invention shown in FIG. 5, dual lumen catheter 100 includes sheath 300 having a substantially circular cross-section and an inner surface 301 with an inner diameter substantially equal to D. Within sheath 300 lies interior tubular element 302 having outer surface 304 and interior surface 320. Outer surface 304 has a diameter equal to D1 whereas inner surface 320 has a diameter equal to d, where d is less than D1. A Filament 336 is wound in a helical path around outer surface 304. A flexible bonding material (not shown) is disposed in region 308 between outer surface 304 and inner surface 301.

The multiple lumen catheter of FIGS. 1-3 can be assembled as follows. A first material is extruded to establish the tubular sheath 46. A second material is also extruded to establish the interior element 47. An axial stretching force is then applied to stretch the interior element 47 in the direction of the central axis A, whereby the outer diameter of the interior element is reduced to be less than D1, the nominal (or "at rest") diameter of the outer surface of the interior element 47. The stretched interior element 47 is then drawn through the interior of at least one filament 36 formed in the shape of a helix. This helical filament has an inner diameter substantially equal to D1. The exterior of the filament-wound interior element is then coated with an adhesive and the sheath 46 is positioned over it. The stretching force on element 47 is then removed. Upon removal of the stretching force from the interior element, the interior element and the filament have intimate contact, thereby establishing a filament-wound, multiple lumen interior element. Useful adhesives include, for example, polyurethane and butyl styrene. Upon curing the adhesive, a multiple lumen, filament-wound catheter 10 is formed. Alternatively, the stretching force may be removed just after the filament is wound, and prior to said the positioning step, the sheath may be expanded by exposing it to freon, permitting easy placement of that sheath over the filament wound interior element.

A formed tip may be produced at the distal end of the catheter. In addition, the proximal end of the catheter may be divided to separated tubular portion including a single lumen.

The invention may be embodied in other specific forms without departing from the spirit and scope thereof. The present embodiments are therefore to be considered in all aspects as illustrative and not restrictive, the scope of the invention being indicated by the appended claims rather than by the foregoing description, and all changes which come within the meaning and range of equivalency of the claims are therefore intended to be embraced therein.

We claim:

1. A multiple lumen catheter comprising:
   (a) an elongated, flexible, tubular element extending about a central axis and including embedded therein at least one filament extending in a helical path about said central axis, wherein the inner surface of said tubular element defines an interior region; and
   (b) an elongated divider element having elongated lateral edges, said lateral edges being integral with, and extending from portions of said inner surface of said tubular element, whereby at least two lumens are defined in said interior region on opposing sides of said divider element;
   wherein said tubular element comprises:
   (a) an elongated, flexible, tubular sheath having a substantially circular cross-section and an inner diameter substantially equal to D;
   (b) an elongated, flexible, tubular interior element having an outer surface, an interior surface, and a substantially circular cross-section, said outer surface having a diameter equal to D1 and said interior surface having a diameter equal to d, where D1 is less than D and d is less than D1, and wherein the interior surface of said interior element forms said inner surface of said tubular element;
   (c) said filament, said filament being wound about said outer surface of said tubular interior element; and
   (d) a flexible bonding material dispose dint he region between the outer surface of said interior element and the inner surface of said sheath.

2. The catheter of claim 1 wherein said divider element is substantially rectangular, whereby two lumens are defined in said interior regions.

3. The catheter of claim 1 wherein said divider element has a substantially Y-shaped cross-section, whereby three lumens are defined in said interior region.

4. The catheter of claim 1 or 2 or 3 wherein said filament comprises a material selected form the group consisting of metal and plastic.

5. The catheter of claim 4 wherein said metallic filament comprises surgical grade stainless steel.

6. The catheter of claim 4 wherein said metallic filament comprises titanium.

7. The catheter of claim 4 wherein said plastic filament comprises polyester.

8. The catheter of claim 4 wherein said plastic filament comprises polyamide.

9. The catheter of claims 1 or 2 or 3 wherein said tubular element comprises a material selected from the group consisting of natural rubber, synthetic rubber, and thermoplastics.

10. The catheter of claim 9 wherein said tubular element comprises silicone.

11. The catheter of claim 9 wherein said tubular element comprises a thermoplastic selected from the group consisting of polyurethane and polyvinylchloride.

12. The catheter of claim 9 wherein said tubular element comprises the synthetic rubber, butyl styrene.

* * * * *